United States Patent
Regan et al.

(10) Patent No.: US 8,917,272 B2
(45) Date of Patent: Dec. 23, 2014

(54) METHODS, APPARATUSES, AND COMPUTER PROGRAM PRODUCTS FOR FACILITATING VISUALIZATION AND ANALYSIS OF MEDICAL DATA

(75) Inventors: Robyn Regan, Lafayette, CO (US); Matthew Walton, Austin, TX (US)

(73) Assignee: McKesson Financial Holdings, Hamilton (BM)

( * ) Notice: Subject to any disclaimer, the term of this patent is extended or adjusted under 35 U.S.C. 154(b) by 727 days.

(21) Appl. No.: 12/570,522

(22) Filed: Sep. 30, 2009

(65) Prior Publication Data

US 2011/0074788 A1     Mar. 31, 2011

(51) Int. Cl.
*G06T 11/20* (2006.01)
*G06T 11/40* (2006.01)
*G06F 19/00* (2011.01)
*G06T 11/00* (2006.01)

(52) U.S. Cl.
CPC ............... *G06T 11/206* (2013.01); *G06T 11/40* (2013.01); *G06T 11/203* (2013.01); *G06F 19/3406* (2013.01); *G06F 19/3418* (2013.01); *G06T 11/00* (2013.01)
USPC ...................... 345/440; 345/440.1; 345/440.2; 345/441; 345/442; 600/501; 600/523

(58) Field of Classification Search
CPC ...... G06T 11/206; G06T 11/203; G06T 11/40
USPC ................ 345/440–442, 629; 607/17–18, 60; 600/509–512, 523, 538, 365, 501
See application file for complete search history.

(56) References Cited

U.S. PATENT DOCUMENTS

| | | | | |
|---|---|---|---|---|
| 4,323,766 | A * | 4/1982 | Brachthauser | 235/89 R |
| 4,896,677 | A * | 1/1990 | Kaneko et al. | 600/509 |
| 5,242,804 | A * | 9/1993 | Bahar et al. | 435/7.93 |
| 5,394,268 | A * | 2/1995 | Lanni et al. | 359/386 |
| 5,410,473 | A * | 4/1995 | Kaneko et al. | 600/523 |
| 5,609,612 | A * | 3/1997 | Plicchi et al. | 607/17 |
| 5,810,011 | A * | 9/1998 | Kunig | 600/481 |
| 5,896,131 | A * | 4/1999 | Alexander | 345/634 |
| 6,038,469 | A * | 3/2000 | Karlsson et al. | 600/512 |
| 6,937,899 | B2 * | 8/2005 | Sheldon et al. | 607/18 |
| 7,139,609 | B1 * | 11/2006 | Min et al. | 607/17 |
| 7,796,798 | B2 * | 9/2010 | Prakash | 382/139 |
| 2002/0120207 | A1 * | 8/2002 | Hoffman | 600/538 |
| 2003/0080962 | A1 * | 5/2003 | Erickson et al. | 345/440 |
| 2004/0095350 | A1 * | 5/2004 | Kamiyama | 345/441 |
| 2004/0102814 | A1 * | 5/2004 | Sorensen et al. | 607/17 |
| 2004/0174818 | A1 * | 9/2004 | Zocchi | 370/241 |
| 2006/0074464 | A1 * | 4/2006 | Subera et al. | 607/60 |

(Continued)

*Primary Examiner* — Jin-Cheng Wang
(74) *Attorney, Agent, or Firm* — Alston & Bird LLP

(57) ABSTRACT

Methods, apparatuses, and computer program products are provided for facilitating visualization and analysis of medical data. A method may include accessing a first set of data points. The method may further include plotting a plurality of data points from the first set of data points on a first graph. The method may additionally include causing the first graph to be displayed. The method may also include accessing a second set of data points. The method may further include plotting a plurality of data points from the second set of data points on a second graph. The method may also include causing the second graph to be displayed overlaying the first graph. At least a portion of the second graph may be semi-transparent such that at least a portion of the first graph is viewable concurrently with the second graph. Corresponding apparatuses and computer program products are also provided.

21 Claims, 10 Drawing Sheets

(56) References Cited

U.S. PATENT DOCUMENTS

| | | | |
|---|---|---|---|
| 2006/0221078 A1* | 10/2006 | Ishizuka | 345/440 |
| 2009/0027394 A1* | 1/2009 | Chuang et al. | 345/440 |
| 2010/0185225 A1* | 7/2010 | Albrecht et al. | 606/191 |
| 2010/0317950 A1* | 12/2010 | Galley et al. | 600/365 |

* cited by examiner

FROM FIG. 6B

| | | | | | FLUIDS & NUTRITION | | |
|---|---|---|---|---|---|---|---|
| | | | | □ x | 24 HOUR INPUT | 4.2 | 0300 |
| | | | | | 24 HOUR OUTPUT | 4.3 | 0300 |
| | | | | | INPUT/ SINCE ADMISSION | 13.8 | 0300 |
| | | | | PRINT | OUTPUT/ SINCE ADMISSION | 13.0 | 0300 |
| | | | | | INPUT | - | 0300 |
| | | | | | IVT | - | 0300 |
| 03/02/09 0305 | | 03/01/09 1132 | | | TT CHTPN | PROMOTE - 20CC/HR | 0300 |
| | | | | | BLOOD PRODUCTS | - | 0300 |
| RESULTS | UNITS | RESULTS | UNITS | RANGE | OUTPUT | | |
| 12.2 | 1000/MM3 | 13.2 | 1000/MM3 | 4.5-11.0 | TOTAL URINE | 0 | 0200 |
| 13.1 | GM/DL | 11 | GM/DL | 11.0-15.5 | URINE RATE □ | 25 | |
| 38.2 | N/A | 34 | N/A | 11.0-45.0 | NQ | - | |
| 87 | N | 86 | N | 85-95 | ELECTROLYTES | | |
| 14 | | 13 | | 12-15 | CA | 8 | 0300 |
| 215 | 1000/MM3 | 180 | 1000/MM3 | 140-160 | MG | 1.6 | 0300 |
| 15 | N/A | 13 | N/A | | PO4 | 5.2 | 0300 |
| 47 | N/A | 41 | N/A | | ENDOCRINE | | |
| 28 | N/A | 33 | N/A | 20-35 | GLUCOSE - CURRENT | 111 | 0300 |
| 2 | N/A | 2 | N/A | 25 | GLUCOSE (HIGH - LOW) | 124 - 98 | 0300 |
| 71 | N/A | 68 | N/A | 65-80 | GI/LIVER | | |
| 4.4 | MILL/COMM | 4.3 | MILL/COMM | 4.15-4.86 | LINES | | |

FROM FIG. 6C

REMINDERS □ x

THERE ARE NO REMINDERS SET.

CREATE REMINDER

Patient Monitoring

*FIG. 6D*

METHODS, APPARATUSES, AND COMPUTER PROGRAM PRODUCTS FOR FACILITATING VISUALIZATION AND ANALYSIS OF MEDICAL DATA

TECHNOLOGICAL FIELD

Embodiments of the present invention relate generally to presentation of medical data and, more particularly, relate to methods, apparatuses, and computer program products for facilitating visualization and analysis of medical data.

BACKGROUND

Clinicians caring for a patient often need to analyze large amounts of patient medical data in order to make decisions about treatment of the patient. Partly as a result of an aging population, clinicians (e.g., doctors, physicians, nurses, therapists, and/or the like) are treating greater numbers of sicker patients having more complex health problems. These sicker patients may face multiple health issues that may be interrelated and thus treatment of one health issue may require consideration of any potential effect on another health issue. Further, response of a sicker patient to a treatment may differ from the response of a patient having fewer health issues to the same treatment. Accordingly, clinicians may need to consult medical data including, for example, patient condition data, patient treatment data, and/or the like, in order to make informed and effective patient treatment decisions.

Currently, clinicians are often forced to consult several independent flow sheets (e.g., printed flow sheets or electronically displayed flow sheets) having simple single line graphs to review patient data for making treatment decisions. Clinicians must then mentally process and compare the data presented by the several flow sheets. With increasing complexity of care for sicker patients, clinicians may be presented with increasing numbers of clinical variables that may make it difficult for clinicians to understand how the variables interrelate with one another. Analyzing the myriad flow sheets to determine how medical data variables interrelate may be quite time consuming. The time consuming nature of this analysis may be quite troubling for busy clinicians responsible for caring for several patients as well as for clinicians faced with making a time-critical treatment decision to treat a patient in failing health. Moreover, the increased complexity and need to consult several flow sheets may increase the risk of introducing medical errors as a clinician may overlook a critical piece of data or may reach an incorrect decision due to the difficulty in analyzing several flow sheets.

BRIEF SUMMARY OF SOME EXAMPLES OF THE INVENTION

Methods, apparatuses, and computer program products are therefore provided for facilitating visualization and analysis of medical data. In this regard, methods, apparatuses, and computer program products are provided that may provide several advantages to clinicians or other users viewing and analyzing medical data. Embodiments of the invention provide for visualization of multiple sets of data points via overlaid graphs. According to some embodiments of the invention, an overlaid graph is semi-transparent such that at least a portion of an underlying graph is viewable concurrently with an overlying graph. In such embodiments, a clinician is enabled to view multiple medical data graphs concurrently to facilitate analysis of medical data for making medical treatment decisions.

Some embodiments of the invention further provide for display of two or more overlaid graphs with each displayed graph sharing one common coordinate axis having a common scale. Each displayed graph of such embodiments may further comprise a respective second coordinate axis having a scale different from a scale of a corresponding second coordinate axis of another displayed graph. These embodiments enable the correlation of the graphs with respect to a first parameter, such as time, on the shared first coordinate axis, while displaying each graph with a second coordinate axis having a scale appropriate for the data points plotted in the respective graph. This display of overlaid graphs having different scales for the respective corresponding second coordinate axes according to some embodiments of the invention enables, for example, the display of medical data points defining values having widely different scales in a correlated and visually friendly manner. Clinicians may then be enabled to view trends in each graph line that might not otherwise be viewable if, for example, all of the graph lines were plotted on a single graph having a single scale due to the possibility that having a coordinate axis scale large enough to accommodate a first graph line defining medical data values of a much greater magnitude than the medical data values defined by a second graph line may make it difficult to discern actual values and trends from viewing the second graph line, which may be displayed in a compressed fashion due to the large coordinate axis scale. Embodiments of the invention therefore enable the correlation of changes in patient condition with changes in patient treatments, thus making a clinician's job easier, and possibly reducing the occurrence of errors in interpretation of medical data.

In a first example embodiment, a method for visually presenting medical data to facilitate analysis of the medical data is provided. The method of this embodiment comprises accessing a first set of data points defining medical data values associated with a patient. The method of this embodiment further comprises plotting a plurality of data points from the first set of data points on a first graph comprising a first coordinate axis and a second coordinate axis. The second coordinate axis has a first scale and each of the plotted plurality of data points from the first set of data points is plotted with respect to the second coordinate axis based at least in part upon the value of the medical data value defined by the data point. The method of this embodiment additionally comprises causing the first graph to be displayed. The method of this embodiment also comprises accessing a second set of data points defining medical data values associated with the patient. The method of this embodiment further comprises plotting a plurality of data points from the second set of data points on a second graph sharing the first coordinate axis with the first graph and further comprising a third coordinate axis. The third coordinate axis has a second scale and each of the plotted plurality of data points from the second set of data points is plotted with respect to the third coordinate axis based at least in part upon the value of the medical data value defined by the data point. The method of this embodiment additionally comprises causing the second graph to be displayed overlaying the first graph. At least a portion of the second graph is semi-transparent such that at least a portion of the first graph is viewable concurrently with the second graph.

In another example embodiment, an apparatus for visually presenting medical data to facilitate analysis of the medical data is provided. The apparatus of this embodiment comprises a processor configured to cause the apparatus to access a first set of data points defining medical data values associated with a patient. The processor of this embodiment is further configured to cause the apparatus to plot a plurality of data points from the first set of data points on a first graph comprising a first coordinate axis and a second coordinate axis. The second coordinate axis has a first scale and each of the plotted plurality of data points from the first set of data points is plotted with respect to the second coordinate axis based at least in part upon the value of the medical data value defined by the data point. The processor of this embodiment is additionally configured to cause the apparatus to cause the first graph to be displayed. The processor of this embodiment is also configured to cause the apparatus to access a second set of data points defining medical data values associated with the patient. The processor of this embodiment is further configured to cause the apparatus to plot a plurality of data points from the second set of data points on a second graph sharing the first coordinate axis with the first graph and further comprising a third coordinate axis. The third coordinate axis has a second scale and each of the plotted plurality of data points from the second set of data points is plotted with respect to the third coordinate axis based at least in part upon the value of the medical data value defined by the data point. The processor of this embodiment is additionally configured to cause the apparatus to cause the second graph to be displayed overlaying the first graph. At least a portion of the second graph is semi-transparent such that at least a portion of the first graph is viewable concurrently with the second graph.

In another example embodiment, a computer program product for visually presenting medical data to facilitate analysis of the medical data is provided. The computer program product includes at least one computer-readable storage medium having computer-readable program instructions stored therein. The computer-readable program instructions may include a plurality of program instructions. Although in this summary, the program instructions are ordered, it will be appreciated that this summary is provided merely for purposes of example and the ordering is merely to facilitate summarizing the computer program product. The example ordering in no way limits the implementation of the associated computer program instructions. The first program instruction of this embodiment is configured for accessing a first set of data points defining medical data values associated with a patient. The second program instruction of this embodiment is configured for plotting a plurality of data points from the first set of data points on a first graph comprising a first coordinate axis and a second coordinate axis. The second coordinate axis has a first scale and each of the plotted plurality of data points from the first set of data points is plotted with respect to the second coordinate axis based at least in part upon the value of the medical data value defined by the data point. The third program instruction of this embodiment is configured for causing the first graph to be displayed. The fourth program instruction of this embodiment is configured for accessing a second set of data points defining medical data values associated with the patient. The fifth program instruction of this embodiment is configured for plotting a plurality of data points from the second set of data points on a second graph sharing the first coordinate axis with the first graph and further comprising a third coordinate axis. The third coordinate axis has a second scale and each of the plotted plurality of data points from the second set of data points is plotted with respect to the third coordinate axis based at least in part upon the value of the medical data value defined by the data point. The sixth program instruction of this embodiment is configured for causing the second graph to be displayed overlaying the first graph. At least a portion of the second graph is semi-transparent such that at least a portion of the first graph is viewable concurrently with the second graph.

In another example embodiment, an apparatus for visually presenting medical data to facilitate analysis of the medical data is provided. The apparatus of this embodiment comprises means for accessing a first set of data points defining medical data values associated with a patient. The apparatus of this embodiment further comprises means for plotting a plurality of data points from the first set of data points on a first graph comprising a first coordinate axis and a second coordinate axis. The second coordinate axis has a first scale and each of the plotted plurality of data points from the first set of data points is plotted with respect to the second coordinate axis based at least in part upon the value of the medical data value defined by the data point. The apparatus of this embodiment additionally comprises means for causing the first graph to be displayed. The apparatus of this embodiment also comprises means for accessing a second set of data points defining medical data values associated with the patient. The apparatus of this embodiment further comprises means for plotting a plurality of data points from the second set of data points on a second graph sharing the first coordinate axis with the first graph and further comprising a third coordinate axis. The third coordinate axis has a second scale and each of the plotted plurality of data points from the second set of data points is plotted with respect to the third coordinate axis based at least in part upon the value of the medical data value defined by the data point. The apparatus of this embodiment additionally comprises means for causing the second graph to be displayed overlaying the first graph. At least a portion of the second graph is semi-transparent such that at least a portion of the first graph is viewable concurrently with the second graph.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the invention in any way. It will be appreciated that the scope of the invention encompasses many potential embodiments, some of which will be further described below, in addition to those here summarized.

BRIEF DESCRIPTION OF THE DRAWING(S)

Having thus described embodiments of the invention in general terms, reference will now be made to the accompanying drawings, which are not necessarily drawn to scale, and wherein:

DETAILED DESCRIPTION

Figure 1:
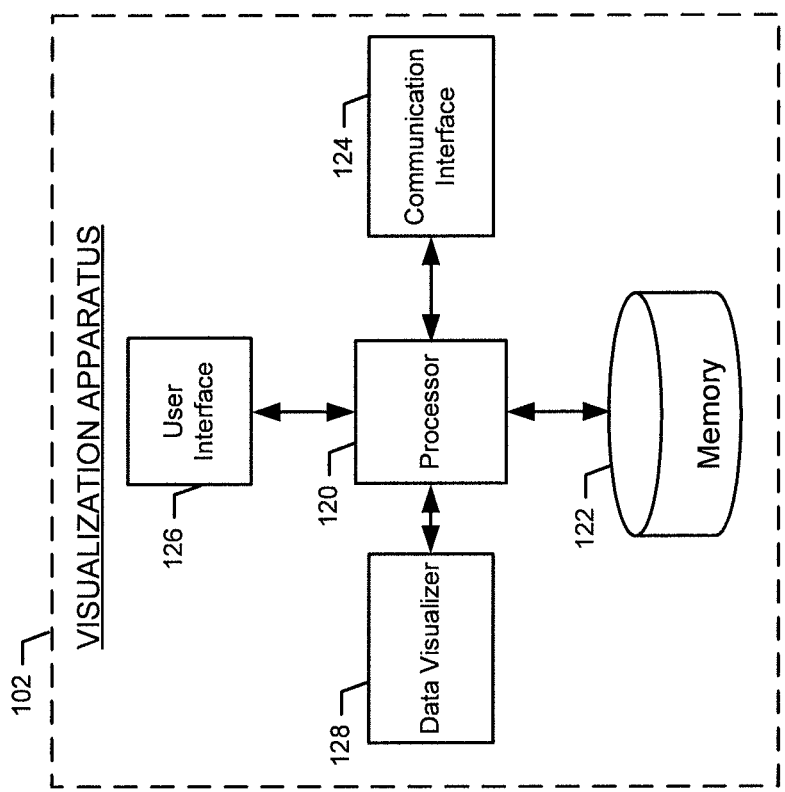
FIG. 1 illustrates an apparatus for facilitating visualization and analysis of medical data according to an exemplary embodiment of the present invention.

Some embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like reference numerals refer to like elements throughout.

FIG. 1 illustrates a visualization apparatus 102 for facilitating visualization and analysis of medical data according to an exemplary embodiment of the present invention. As used herein, "exemplary" merely means an example and as such represents one example embodiment for the invention and should not be construed to narrow the scope or spirit of the invention in any way. It will be appreciated that the scope of the invention encompasses many potential embodiments in addition to those illustrated and described herein. As such, while FIG. 1 illustrates one example of a configuration of a visualization apparatus for facilitating visualization and analysis of medical data, numerous other configurations may also be used to implement embodiments of the present invention.

The visualization apparatus 102 may be embodied as a server, desktop computer, laptop computer, mobile terminal, mobile computer, mobile phone, mobile communication device, audio/video player, television device, network node, multiple computing devices in communication with each other, any combination thereof, and/or the like.

In an exemplary embodiment the visualization apparatus 102 includes various means, such as a processor 120, memory 122, communication interface 124, user interface 126, and data visualizer 128 for performing the various functions herein described. These means of the visualization apparatus 102 as described herein may be embodied as, for example, circuitry, hardware elements (e.g., a suitably programmed processor, combinational logic circuit, and/or the like), a computer program product comprising computer-readable program instructions (e.g., software or firmware) stored on a computer-readable medium (e.g. memory 122) that is executable by a suitably configured processing device (e.g., the processor 120), or some combination thereof.

The processor 120 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an ASIC (application specific integrated circuit) or FPGA (field programmable gate array), or some combination thereof. Accordingly, although illustrated in FIG. 1 as a single processor, in some embodiments the processor 120 comprises a plurality of processors. The plurality of processors may be embodied on a single computing device or may be distributed across a plurality of computing devices collectively configured to function as the visualization apparatus 102. The plurality of processors may be in operative communication with each other and may be collectively configured to perform one or more functionalities of the visualization apparatus 102 as described herein. In an exemplary embodiment, the processor 120 is configured to execute instructions stored in the memory 122 or otherwise accessible to the processor 120. These instructions, when executed by the processor 120, may cause the visualization apparatus 102 to perform one or more of the functionalities of the visualization apparatus 102 as described herein. As such, whether configured by hardware or software methods, or by a combination thereof, the processor 120 may comprise an entity capable of performing operations according to embodiments of the present invention while configured accordingly. Thus, for example, when the processor 120 is embodied as an ASIC, FPGA or the like, the processor 120 may comprise specifically configured hardware for conducting one or more operations described herein. Alternatively, as another example, when the processor 120 is embodied as an executor of instructions, such as may be stored in the memory 122, the instructions may specifically configure the processor 120 to perform one or more algorithms and operations described herein.

The memory 122 may include, for example, volatile and/or non-volatile memory. Although illustrated in FIG. 1 as a single memory, the memory 122 may comprise a plurality of memories. The plurality of memories may be embodied on a single computing device or distributed across a plurality of computing devices. The memory 122 may comprise volatile memory, non-volatile memory, or some combination thereof. In this regard, the memory 122 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof. The memory 122 may be configured to store information, data, applications, instructions, or the like for enabling the visualization apparatus 102 to carry out various functions in accordance with exemplary embodiments of the present invention. For example, in at least some embodiments, the memory 122 is configured to buffer input data for processing by the processor 120. Additionally or alternatively, in at least some embodiments, the memory 122 is configured to store program instructions for execution by the processor 120. The memory 122 may store information in the form of static and/or dynamic information. This stored information may be stored and/or used by the data visualizer 128 during the course of performing its functionalities.

The communication interface 124 may be embodied as any device or means embodied in circuitry, hardware, a computer program product comprising computer readable program instructions stored on a computer readable medium (e.g., the memory 122) and executed by a processing device (e.g., the processor 120), or a combination thereof that is configured to receive and/or transmit data from/to another device, such as, for example, a server, a user terminal (e.g., the user terminal 206 illustrated in FIG. 2), a data source (e.g., the data source 306 illustrated in FIG. 3), and/or the like. In at least one embodiment, the communication interface 124 is at least partially embodied as or otherwise controlled by the processor 120. In this regard, the communication interface 124 may be in communication with the processor 120, such as via a bus. The communication interface 124 may include, for example, an antenna, a transmitter, a receiver, a transceiver and/or supporting hardware or software for enabling communications with another computing device. The communication interface 124 may be configured to receive and/or transmit data using any protocol that may be used for communications between computing devices. The communication interface 124 may additionally be in communication with the memory 122, user interface 126, and/or data visualizer 128, such as via a bus.

The user interface 126 may be in communication with the processor 120 to receive an indication of a user input and/or to provide an audible, visual, mechanical, or other output to a user. As such, the user interface 126 may include, for example, a keyboard, a mouse, a joystick, a display, a touch screen display, a microphone, a speaker, and/or other input/output mechanisms. In embodiments wherein the visualization apparatus 102 is embodied as a server, aspects of the user interface 126 may be reduced or the user interface 126 may even be eliminated. Alternatively, such as in embodiments wherein the visualization apparatus 102 is embodied as a server, at least some aspects of the user interface 126 may be embodied on an apparatus used by a user that is in communication with the visualization apparatus 102, such as for example, the user terminal 206 illustrated in FIG. 2. The user interface 126 may provide means for a user to select medical data for display and view displayed medical data. The user interface 126 may be in communication with the memory 122, communication interface 124, and/or data visualizer 128, such as via a bus.

The data visualizer 128 may be embodied as various means, such as circuitry, hardware, a computer program product comprising computer readable program instructions stored on a computer readable medium (e.g., the memory 122) and executed by a processing device (e.g., the processor 120), or some combination thereof and, in one embodiment, is embodied as or otherwise controlled by the processor 120. In embodiments wherein the data visualizer 128 is embodied separately from the processor 120, the data visualizer 128 may be in communication with the processor 120. The data visualizer 128 may further be in communication with one or more of the memory 122, communication interface 124, or user interface 126, such as via a bus.

Figure 2:
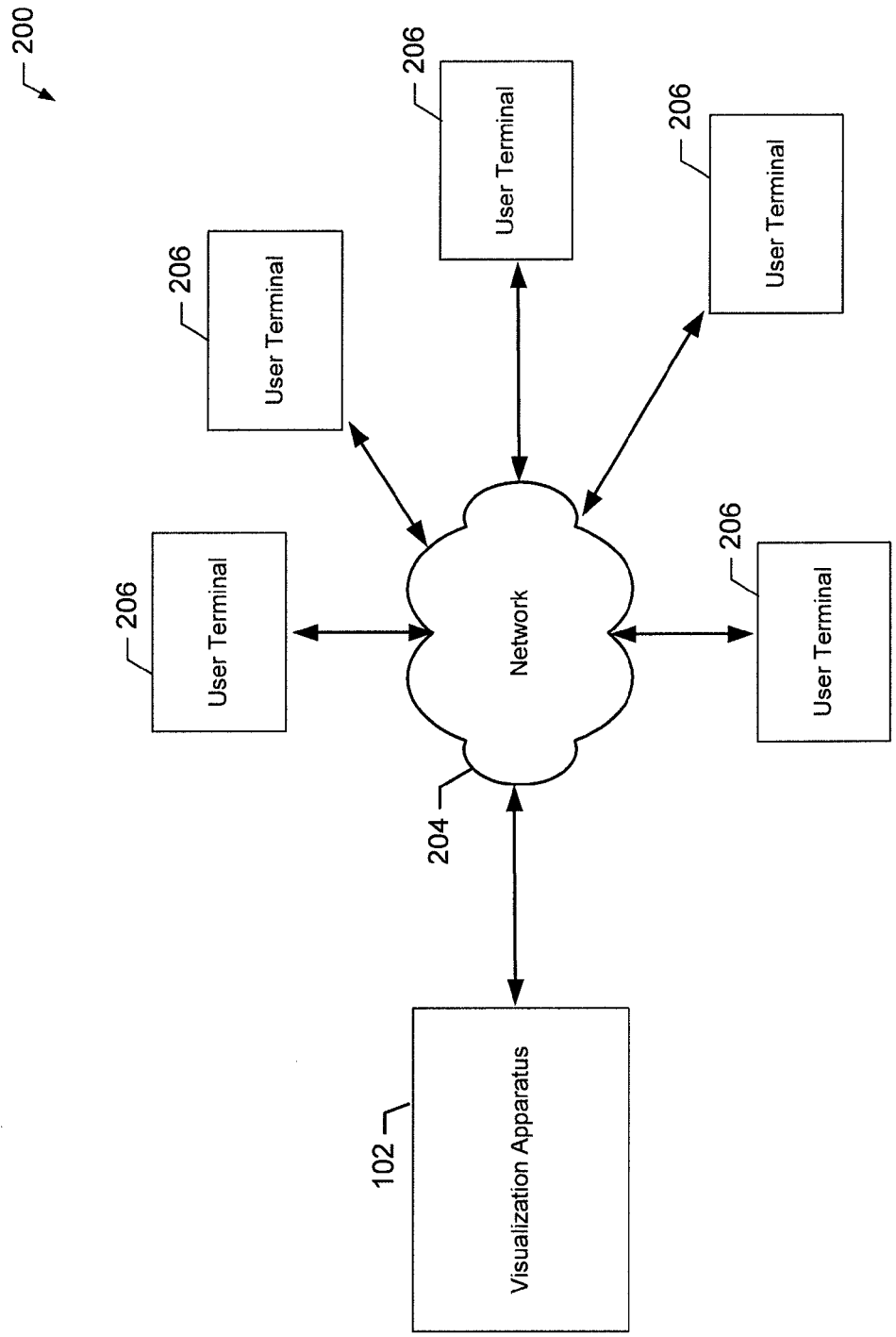
FIG. 2 illustrates a system for facilitating visualization and analysis of medical data according to an exemplary embodiment of the present invention.

FIG. 2 illustrates a system 200 for facilitating visualization and analysis of medical data according to an exemplary embodiment of the present invention. In this regard, FIG. 2 illustrates a system wherein the visualization apparatus 102 comprises and/or is embodied as one or more servers in communication with one or more remote user terminals 206 over a network 204. The network 204 may comprise a wireless network (e.g., a cellular network, wireless local area network, wireless personal area network, wireless metropolitan area network, and/or the like), a wireline network, or some combination thereof, and in some embodiments comprises the internet. The user terminal 206 may comprise any device configured for use by a user to access medical data visualization services provided by the visualization apparatus 102 over the network 204. In this regard, the user terminal 206 may be embodied as a desktop computer, laptop computer, mobile terminal, mobile computer, mobile phone, mobile communication device, audio/video player, television device, any combination thereof, and/or the like.

In embodiments, such as that depicted in FIG. 2, wherein a user terminal 206 is remote from the visualization apparatus 102, elements of the visualization apparatus 102 that were described with respect to FIG. 1 and functionality attributed thereto may be distributed between the visualization apparatus 102 and user terminal 206. For example, the data visualizer 128 may be distributed between the visualization apparatus 102 and user terminal 206, such that functionality attributed to the data visualizer 128 may be performed by the visualization apparatus 102 and/or by the user terminal 206. Additionally or alternatively, where the data visualizer 128 is said to be configured to cause a graph or other medical data to be displayed, it will be appreciated that the data visualizer 128 may be configured to cause the graph and/or other medical data to be displayed on a display connected to the visualization apparatus 102 and/or may be configured to cause transmission of the data to be displayed via the communication interface 124 to a user terminal 206 such that the graph and/or other medical data may be displayed on a display connected to or embodied on the user terminal 206. Similarly, where receipt of a selection of medical data for display, receipt of a selection for adjustment of displayed medical data, and/or receipt of other user input is described, it will be appreciated that the user may be providing the selection or input via the user interface 126 and/or may be interacting with a user terminal 206 such that the input and/or selection is transmitted from the user terminal 206 to the visualization apparatus 102, where it may be received by the communication interface 124 and/or data visualizer 128. Further, program instructions, medical data, and/or other data said to be stored in the memory 122 may be stored at the visualization apparatus 102 and/or may be stored on the user terminal 206.

Accordingly, embodiments of the invention wherein the visualization apparatus is part of the system 200 enable remote access to medical data formatted to facilitate visualization and analysis by the visualization apparatus 102 at a user terminal 206. This remote access may enable, for example, a clinician to access and analyze visual medical data formatted by the visualization apparatus 102 from any location including, for example, a computer located in the clinician's office, the clinician's mobile computing device, and/or the like.

Figure 3:
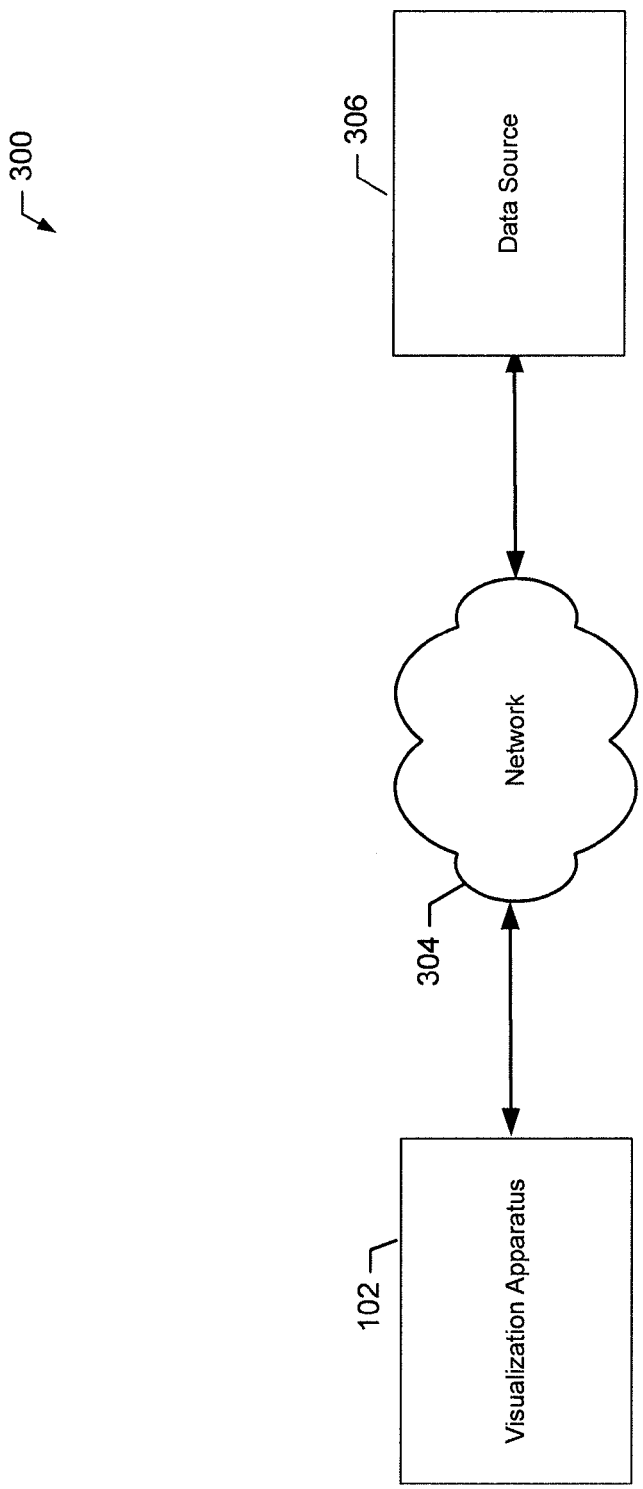
FIG. 3 illustrates a system for facilitating visualization and analysis of medical data according to an exemplary embodiment of the present invention.

FIG. 3 illustrates a system 300 for facilitating visualization and analysis of medical data according to an exemplary embodiment of the present invention. In this regard, FIG. 3 illustrates a system wherein the visualization apparatus 102 is in communication with one or more data sources 306 over a network 304. The network 304 may comprise a wireless network (e.g., a cellular network, wireless local area network, wireless personal area network, wireless metropolitan area network, and/or the like), a wireline network, or some combination thereof, and in some embodiments comprises the internet. Additionally or alternatively, the network 304 may comprise a body area network (BAN), which may be configured in accordance with standards set forth by the Institute of Electrical and Electronics Engineers (IEEE) 802.15.6 task group. In some embodiments, the network 304 may comprise the network 204. In this regard, although not illustrated in FIG. 3, the system 300 may further comprise one or more user terminals 206 as illustrated and described in connection with the system 200 of FIG. 2.

The data source 306 may comprise any computing device comprising a memory configured to store medical data such that it is accessible by the visualization apparatus 102 over the network 304. Additionally or alternatively, the data source 306 may comprise a real time data source configured to monitor patient vital signs and transmit monitored vital signs data over the network 304 such that it is accessible by the visualization apparatus 102. In this regard, the data source 306 may comprise, for example, a network attached storage device, a server, a desktop computer, laptop computer, mobile terminal, mobile computer, mobile phone, mobile communication device, audio/video player, a medical monitoring device or vital signs sensor (e.g., a sensor or monitor configured for operation on a body area network), any combination thereof, and/or the like.

In one embodiment, the data source 306 is embodied as a fact repository, such as that implemented by the McKesson® Predictive Care infrastructure for use in the Care Progression product. The fact repository may be embodied by a computing device, such as a personal computer, a server, or the like. Regardless of its particular implementation, the fact repository generally includes one or more processors and one or more memory devices, such as random access memory, in communication with the processor(s). Accordingly, performance of various functions by the fact repository may, in one embodiment, entail the performance of those functions by the processor of the fact repository. The processor of the fact repository may be configured to receive data regarding one or more patients. The data may be provided in various manners and, in one embodiment, is provided via a bus (not illustrated) and/or over the network 304 from, for example, one or more core clinical systems, such as the Horizon Expert Documentation™, Horizon Expert Orders™ and/or Horizon Adm-nRx™ systems. In one example, however, a healthcare professional, such as a physician or a nurse, may collect new or updated data regarding a patient and may provide the data to the system via a user station. Upon receipt of the patient data, the fact repository may process the data and, in some instances, may distribute and/or store a representation of the data.

In one embodiment, the fact repository may enhance the patient data through associations with clinical concepts to form structured data. As a result of the associations with clinical concepts, the fact repository may process the patient data in various manners, such as by transforming the patient data to a standard representation. For example, in instances in which the data represents the patient's temperature, the fact repository may be configured to transform the temperature from a simple string representation, such as 101.9 F, to a strongly-typed internal, floating-point representation of the value. Through associations with clinical terms and rules related to the clinical terms, the fact repository may also determine one or more attributes associated with the transformed value. For example, the fact repository may, in the foregoing example, compare the transformed temperature value to a normal range of temperature values and determine if the patient's temperature is high, normal or low. These attributes may then be stored along with or otherwise in association with the patient data.

The fact repository may then process the structured data in accordance with rules associated with clinical concepts in order to further characterize and specify the nature of the patient data. For example, the fact repository may be configured to determine trends with respect to the patient data. The definition of a trend may be dependent upon the type of patient data. For example, with respect to body temperature, three consecutive body temperature recordings above the normal range within the preceding 12 hours may define a trend that creates an additional clinical fact that may be stored in addition to the underlying patient data. This patient data, attributes related to the patient data, clinical facts created by analysis of the patient data by the fact repository, trends noted through analysis of the patient data by the fact repository, and/or other patient data may be stored on a memory device of the fact repository. Accordingly, the visualization apparatus 102 may be configured to access medical data and/or receive medical data from a fact repository over the network 304.

Embodiments such as that depicted in FIG. 3 wherein the visualization apparatus 102 is in communication with one or more data sources 306 over the network 304 facilitate access by the visualization apparatus 102 to a wide range of remotely stored and/or remotely gathered medical data. This accessed remotely stored/gathered medical data may then be formatted to facilitate visualization and analysis of the accessed medical data by the data visualizer 128 as will be further described herein. Accordingly, it will be appreciated that when the data visualizer 128 is described herein to access medical data from the memory 122, accessing data from the memory 122 is provided merely for purposes of example and the data visualizer 128 may be configured to access medical data from the memory 122 and/or from a data source 306.

In some embodiments, the data visualizer 128 is configured to determine a selection of a first set of data points (e.g., medical data points) for plotting on a first graph. The determined selection may comprise a user input received via the user interface 126 and/or communication interface 124. The selection may comprise, for example, selection of a particular set of data points via a graphical user interface. Additionally or alternatively, the selection may comprise a default selection of a set of data points that the data visualizer 128 may be configured to access and display. The selected first set of data points may define, for example, medical data values associated with a patient. It will be appreciated, however, that medical data values are provided for purposes of example and not by way of limitation. Accordingly, where medical data values are mentioned herein, other data values may be substituted and embodiments of the invention may be applied outside of the medical field. These medical data values may comprise, for example, medical data values related to a condition of the patient (e.g., blood pressure values, oxygen saturation percentage values, body temperature values, pulse rate values, heart rate values, respiratory rate values, lab result values, patient reported values, central venous pressure values, internal pressure measurement values, and/or similar values of the patient), medical data values related to treatment administered to the patient (e.g., ventilator settings, quantity of a medication administered to the patient, medication drip settings, and/or similar values related to treatment administered to the patient), medical data values related to inputs (e.g., intravenous fluids, transfused blood, tube feeding (TPN), and/or the like that go into the patient), medical data values related to outputs (e.g., urine, stool, chest tube drainage, and/or the like that are evacuated or otherwise come out of the patient), and/or the like. The medical data values defined by the data points may be associated with a time at which the medical data value defined by the data point was captured, such as, for example, through measurement or monitoring of the patient with a medical monitoring device.

In some embodiments, the data visualizer 128 is configured to access the first set of data points, such as from the memory 122. The data visualizer 128 may then plot a plurality of data points from the first set of data points on a first graph. The first graph may comprise a first coordinate axis (e.g., an x-axis) and a second coordinate axis (e.g., a y-axis), each having a scale. The data visualizer 128 may be configured to determine the scale of the coordinate axes based at least in part upon the values of medical data values defined by the plotted data points. Additionally or alternatively, the data visualizer 128 may be configured to determine the scale of the coordinate axes based at least in part upon user input. The data visualizer 128 may be configured to plot each of the plotted data points with respect to the second coordinate axis based at least in part upon the value of the medical data value defined by the data point. In embodiments wherein the medical data value defined by a data point is associated with a time at which the medical data value was captured, the first coordinate axis may define a period of time and the data visualizer 128 may be configured to plot the data point with respect to the first axis based at least in part upon the time at which the medical data value defined by the data point was captured.

Figure 4:
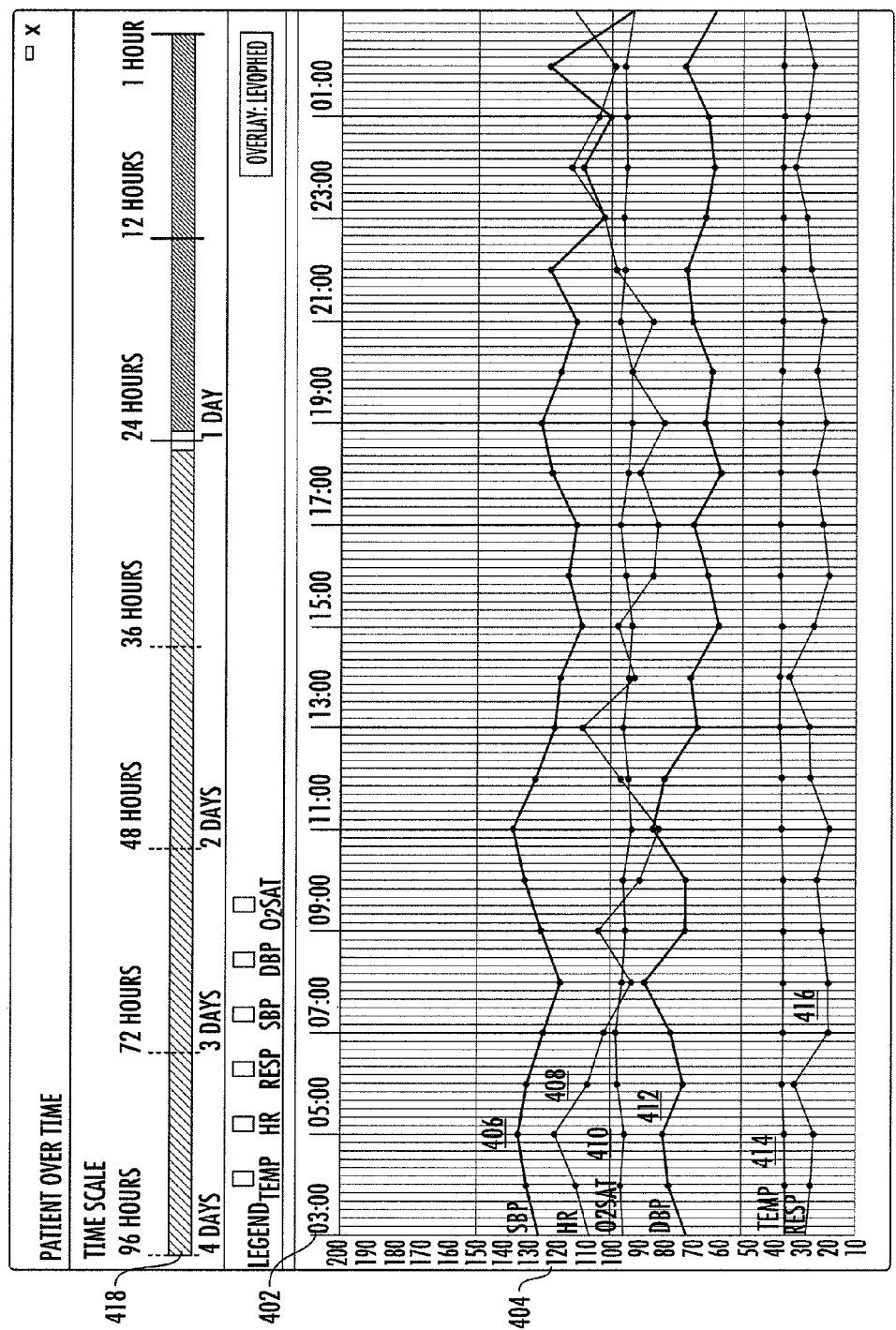
FIG. 4 illustrates a screenshot of a graph comprising plotted medical data points according to an exemplary embodiment of the invention.

The data visualizer 128 is further configured in some embodiments of the invention to cause the first graph to be displayed. FIG. 4 illustrates a screenshot of a displayed graph comprising plotted data points according to an exemplary embodiment of the invention. The graph of FIG. 4 comprises a first coordinate axis 402 defining a period of time defined in 24 hour time having a scale range from 3:00 on a first day to 3:00 on the subsequent day with a scale increment of two hours. The graph of FIG. 4 further comprises a second coordinate axis 404 having a scale range between 10 and 200 with a scale increment of 10. The graph of FIG. 4 also comprises a plurality of plotted graph lines comprised of plotted data points. The plurality of graph lines plotted in FIG. 4 comprises a graph line 406 comprising data points defining systolic blood pressure data values, a graph line 408 comprising data points defining heart rate data values, a graph line 410 comprising data points defining oxygen saturation percentage data values, a graph line 412 defining diastolic blood pressure data values, a graph line 414 defining body temperature data values, and a graph line 416 defining respiratory rate data values. Accordingly, it will be appreciated that while plotting a single set of data points on the first graph was previously described, a plurality of graph lines comprised of multiple accessed sets of data points may be plotted on the first graph by the data visualizer 128 in accordance with various embodiments of the invention.

In some embodiments, the data visualizer 128 is configured to further determine a selection of a second set of data points (e.g., medical data points) for plotting on a second graph. The determined selection may comprise a user input received via the user interface 126 and/or communication interface 124. The selection may comprise, for example, selection of a particular set of data points via a graphical user interface. Additionally or alternatively, the selection may comprise a default selection of a set of data points that the data visualizer 128 may be configured to access and display. The selected second set of data points may define, for example, medical data values associated with a patient. These medical data values may comprise, for example, medical data values related to a condition of the patient (e.g., blood pressure values, oxygen saturation percentage values, body temperature values, pulse rate values, heart rate values, respiratory rate values, lab result values, patient reported values, central venous pressure values, internal pressure measurement values, and/or similar values of the patient), medical data values related to treatment administered to the patient (e.g., ventilator settings, quantity of a medication administered to the patient, medication drip settings, and/or similar values related to treatment administered to the patient), medical data values related to inputs (e.g., intravenous fluids, transfused blood, tube feeding (TPN), and/or other liquids that go into the patient), medical data values related to outputs (e.g., urine, stool, chest tube drainage, and/or the like that are evacuated or otherwise come out of the patient), and/or the like. The medical data values defined by the data points may be associated with a time at which the medical data value defined by the data point was captured, such as, for example, through measurement or monitoring of the patient with a medical monitoring device.

The data visualizer 128 is configured in some embodiments to access the second set of data points, such as from the memory 122. The data visualizer 128 may then plot a plurality of data points from the second set of data points on a second graph. The second graph may comprise a first coordinate axis (e.g., an x-axis) shared with the first graph. In this regard, medical data points plotted on the first and second graphs may be correlated with respect to a parameter, such as, for example, time, the value of which is defined by the first coordinate axis. The second graph may further comprise a third coordinate axis (e.g., a y-axis) corresponding to the second coordinate axis of the first graph (e.g., having the same orientation), but having a different scale than the second coordinate axis of the first graph. The data visualizer 128 may be configured to determine the scale of the third coordinate axis based at least in part upon the values of medical data values defined by the plotted data points. Additionally or alternatively, the data visualizer 128 may be configured to determine the scale of the third coordinate axis based at least in part upon user input. The data visualizer 128 may be configured to plot each of the plotted data points with respect to the third coordinate axis based at least in part upon the value of the medical data value defined by the data point. In embodiments wherein the medical data value defined by a data point is associated with a time at which the medical data value was captured and the first coordinate axis defines a period of time, the data visualizer 128 may be configured to plot the data point with respect to the first axis based at least in part upon the time at which the medical data value defined by the data point was captured such that the plotted data points of the first and second graphs are time correlated to facilitate analysis of trends and/or cause and effect relationships between plotted medical data values by a clinician.

Figure 5:
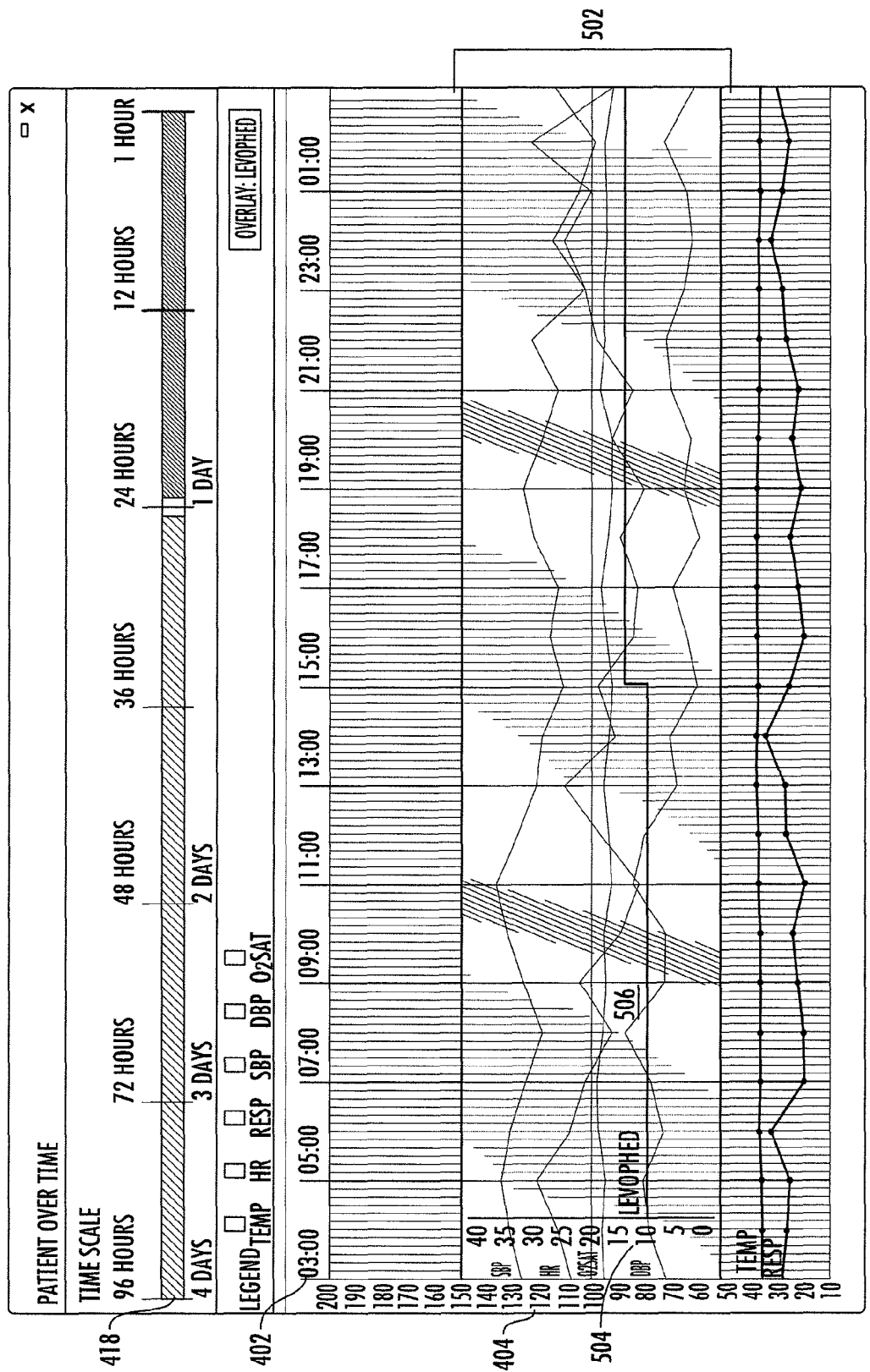
FIG. 5 illustrates a screenshot of an overlaid graph comprising plotted medical data points according to an exemplary embodiment of the invention.

The data visualizer 128 is further configured in some embodiments to cause the second graph to be displayed overlaying the first graph. At least a portion of the second graph may be semi-transparent such that at least a portion of the underlying first graph is viewable concurrently with the second graph to facilitate analysis of trends and/or cause and effect relationships between plotted medical data values by a clinician. In this regard, FIG. 5 illustrates a screenshot of an overlaid graph 502 comprising plotted medical data points forming the graph line 506 according to an exemplary embodiment of the invention. As may be seen in FIG. 5, the overlaid graph 502 is overlying the graph illustrated in FIG. 4 and is semi-transparent such that the underlying graph is viewable concurrently with the overlaid graph 502. The overlaid graph 502 shares the coordinate axis 402 with the underlying graph. However, the graph 502 comprises the coordinate axis 504, which corresponds to the coordinate axis 404 (e.g., having the same orientation), but has a different scale than the coordinate axis 404. In this respect, the coordinate axis 504 has a scale appropriate to the medical data values plotted on the graph line 506. In this regard, the coordinate axis 506 has a scale range between 0 and 40 with a scale increment of 5, thus allowing for a much less compressed display of the graph line 506 than if the graph line 506 were graphed with respect to a coordinate axis having the scale of the coordinate axis 404, which may facilitate easier analysis of trends in the data points plotted in the graph line 506. It will be appreciated that while the overlaid graph 502 comprises only a single graph line, the data visualizer 128 may be configured to plot a plurality of graph lines on an overlaid graph in accordance with embodiments of the invention. Further, in some embodiments, the data visualizer 128 may be configured to overlay a plurality of graphs over a first base graph, each of which may comprise a coordinate axis having a different scale from a corresponding coordinate axis of other graphs, on the first graph.

The displayed graph(s) may comprise and/or be displayed within an interface enabling a user to adjust a scale of one or more of the coordinate axes of the graph(s) so as to change the field of view displayed by the graph(s). In the embodiment illustrated in FIGS. 4 and 5, for example, the displayed graph comprises a slider bar 418 enabling a user an interface enabling a user to adjust the window of time displayed on the coordinate axis 402 from as much as 96 hours (4 days) to as little as 1 hour so that the clinician may analyze trends over varying lengths of time.

In some embodiments, a user may provide an indication over the interface to reorder the overlaid graph layers (e.g., move the overlaid graph to the back and bring the base graph to the front). The data visualizer 128 may accordingly be configured to reorder the overlaid graph layers based upon the user input and cause the reordered overlaid graph layers to be displayed. Additionally or alternatively, some embodiments may allow a user to move a graphed set of data points from one graph to another and/or to a new overlay graph. In this regard, a user may select to move a set of data points graphed on a first graph underlying a second graph to the overlying second graph or to a new overlay graph. Accordingly, the data visualizer 128 may be configured to re-plot the set of data points on the second graph and/or on a third graph overlaying the first and second graphs and cause the adjusted graphs to be displayed.

In some embodiments, a clinician or other user is enabled to select a plotted data point, such as by selecting a point on a plotted graph line with a graphic on-screen cursor or other selection means. Such a selection may, for example, comprise hovering a cursor over the data point, clicking on the data point, other selection means or methods, and/or the like. The data visualizer 128 may be configured to determine the selection of the plotted data point. In response to determining the selection of the plotted data point, the data visualizer 128 may determine the medical data value defined by the selected plotted data point and cause the determined medical data value to be displayed.

Accordingly, through display of overlaying graphs having corresponding coordinate axes of varying scales a clinician may be enabled to analyze any correlation between medical data displayed in the first graph and second graph to make diagnosis and treatment decisions. For example, one of the first and second graphs may comprise a graph line(s) comprising data points defining medical data values related to a condition of the patient and the other graph may comprise a graph line(s) comprising data points defining medical data values related to a treatment administered to the patient. The clinician may then concurrently view the two graphs to ascertain the effect of treatment administered to the patient on the patient's condition.

Figure 6A:
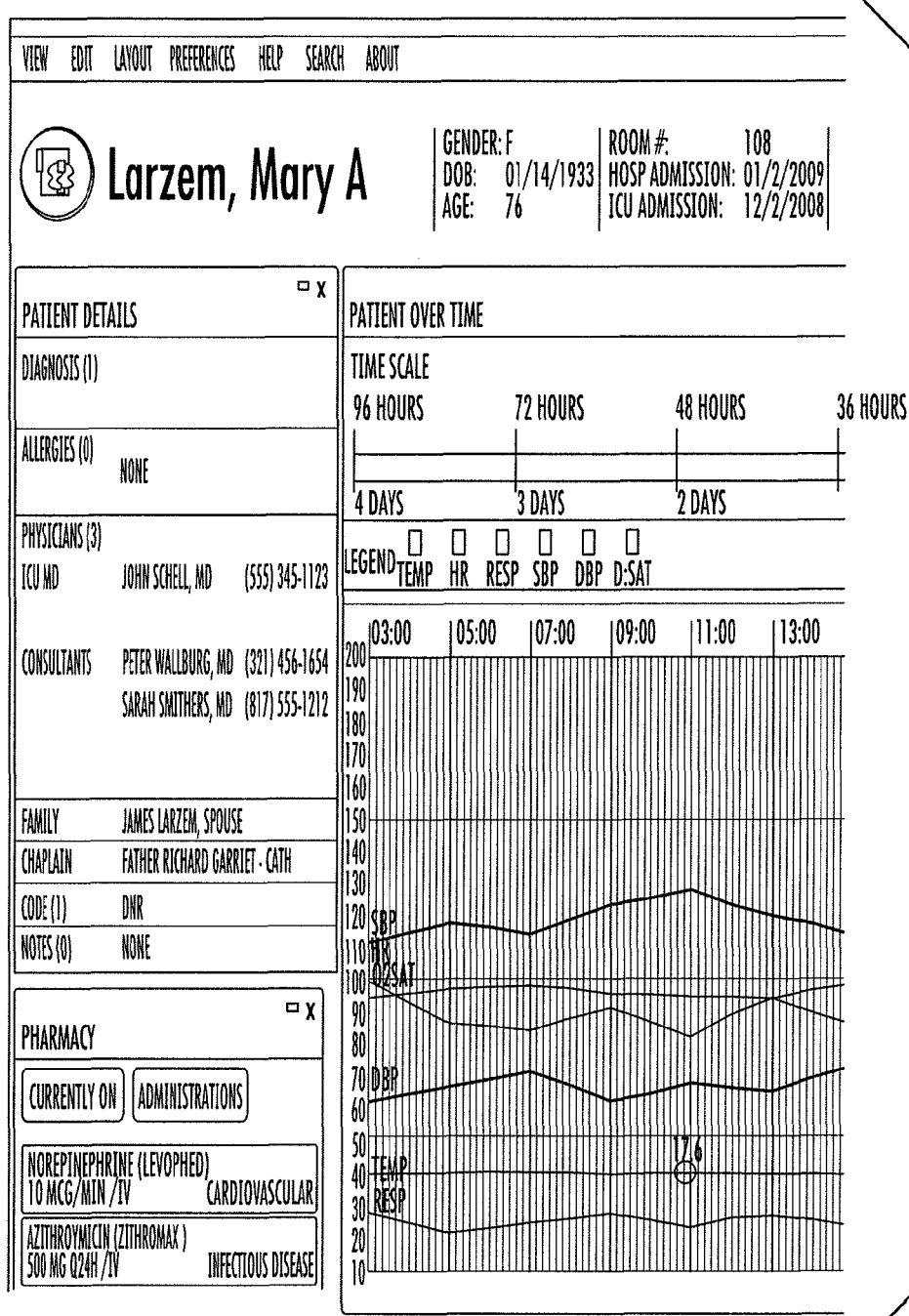
FIG. 6 illustrates a screenshot of medical data displayed according to an exemplary embodiment of the invention.
Figure 6B:
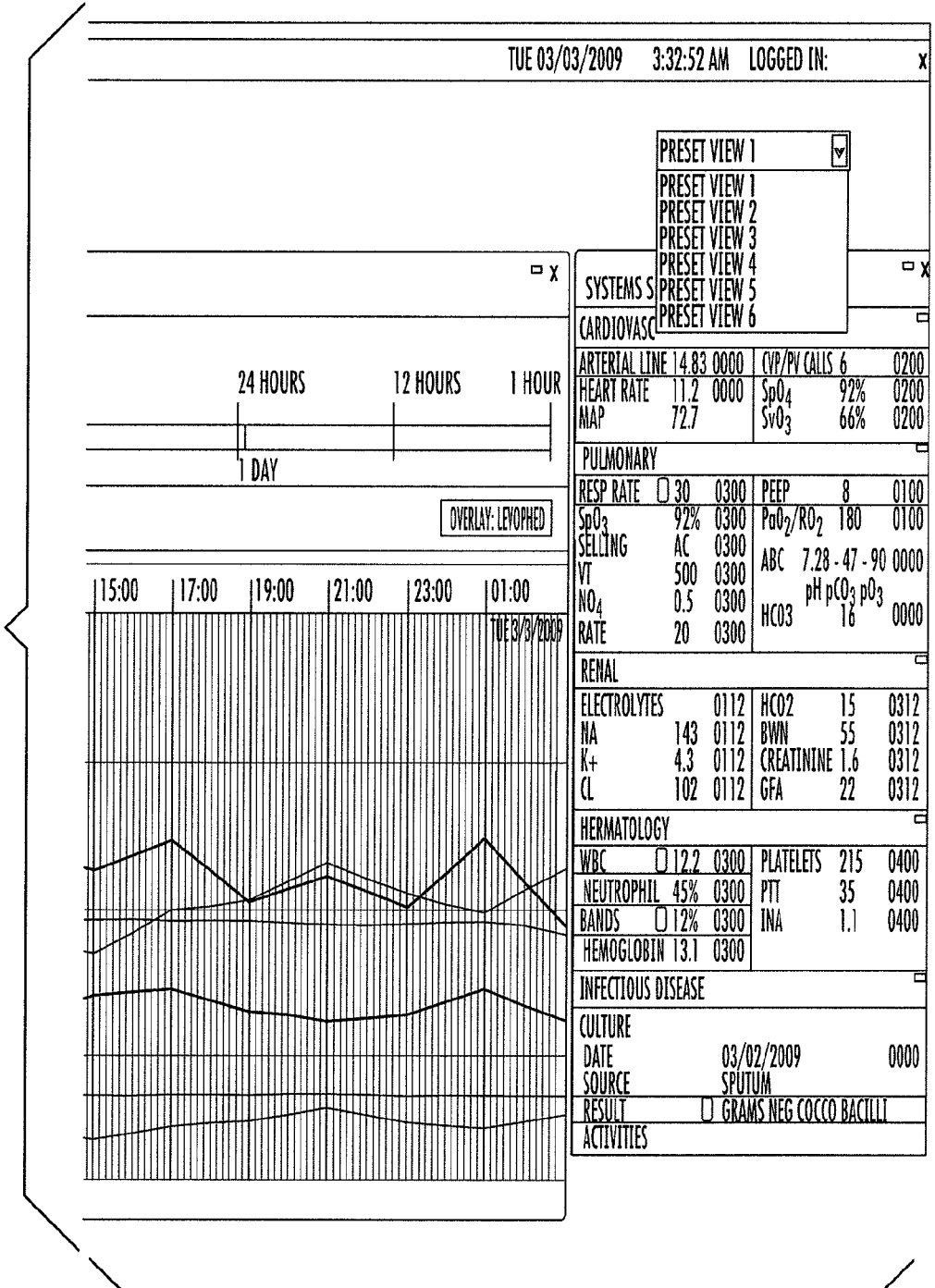
Figure 6C:

In some embodiments of the invention, the data visualizer 128 is configured to cause additional medical data associated with a patient to be displayed concurrently with one or more graphs. This additional medical data may comprise, for example, patient demographic data (e.g., gender, age, date of birth, weight, hospital admission date, length of stay, and/or the like), patient details (e.g., a list of medical problems of the patient, a list of allergies of the patient, information about responsible clinicians caring for the patient, family contact information for the patient, any standing patient care orders, patient notes, and/or the like), information about current patient medications and/or recent medication administrations, patient lab results, medical imaging results (e.g., radiology reports and images for the patient), and/or other medical data associated with the patient. This additional displayed medical data may further facilitate clinician analysis of graphed medical data. In this regard, FIG. 6 illustrates a screenshot of additional medical data displayed in conjunction with a graph according to an exemplary embodiment of the invention. It will be appreciated, however, that the selection and arrangement of medical data displayed in FIG. 6 is merely for purposes of example and not by way of limitation.

Figure 7:
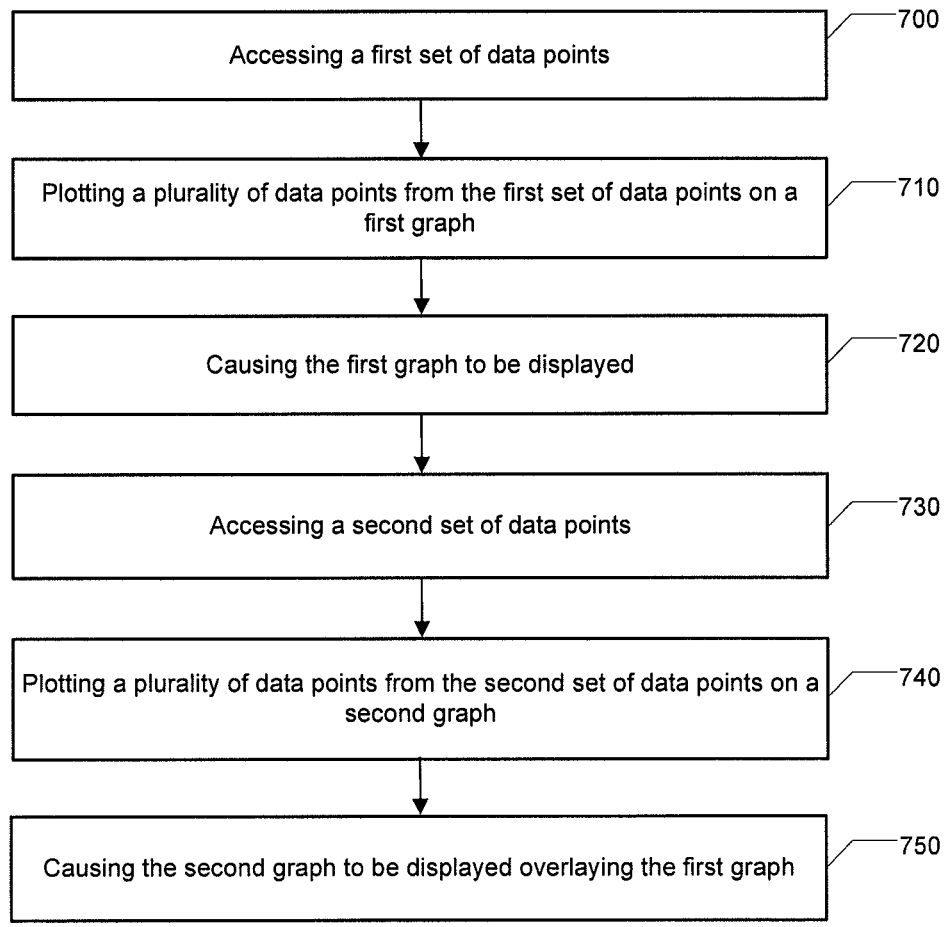
FIG. 7 illustrates a flowchart according to an exemplary method for facilitating visualization and analysis of medical data according to an exemplary embodiment of the invention.

FIG. 7 illustrates a flowchart according to an exemplary method for facilitating visualization and analysis of medical data according to an exemplary embodiment of the invention. The method may include the data visualizer 128 accessing a first set of data points, at operation 700. The first set of data points may define medical data values associated with a patient. Operation 710 may comprise the data visualizer 128 plotting a plurality of data points from the first set of data points on a first graph. The first graph may comprise a first coordinate axis and a second coordinate axis. The second coordinate axis may have a first scale and each of the plotted plurality of data points from the first set of data points may be plotted with respect to the second coordinate axis based at least in part upon the value of the medical data value defined by the data point. The data visualizer 128 may then cause the first graph to be displayed, at operation 720.

Operation 730 may comprise the data visualizer 128 accessing a second set of data points. The second set of data points may define medical data values associated with the patient. The data visualizer 128 may then plot a plurality of data points from the second set of data points on a second graph, at operation 740. The second graph may share the first coordinate axis with the first graph and may further comprise a third coordinate axis. The third coordinate axis may correspond to the second coordinate axis of the first graph, but may have a second scale differing from the first scale of the second coordinate axis. Each of the plotted plurality of data points from the second set of data points may be plotted with respect to the third coordinate axis based at least in part upon the value of the medical data value defined by the data point. Operation 750 may then comprise the data visualizer 128 causing the second graph to be displayed overlaying the first graph. At least a portion of the second graph may be semi-transparent such that at least a portion of the first graph is viewable concurrently with the second graph.

FIG. 7 is a flowchart of a system, method, and computer program product according to exemplary embodiments of the invention. It will be understood that each block or step of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices of a server, desktop computer, laptop computer, mobile computer, or other computing device (e.g., the visualization apparatus 102, user terminal 206, data source 306, combination thereof, and/or the like) and executed by a processor (e.g., the processor 120) in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s) or step(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s) or step(s). The computer program instructions of one or more computer program products may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the flowchart block(s) or step(s).

Accordingly, blocks or steps of the flowchart support combinations of means for performing the specified functions and combinations of steps for performing the specified functions. It will also be understood that one or more blocks or steps of the flowchart, and combinations of blocks or steps in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processor may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

As such, then, some embodiments of the invention provide several advantages to clinicians and other users tasked with analyzing medical data. Embodiments of the invention further provide for display of two or more overlaid graphs with each displayed graph sharing one common coordinate axis having a common scale. Each displayed graph of such embodiments may further comprise a respective second coordinate axis having a scale different from a scale of a corresponding second coordinate axis of another displayed graph. These embodiments enable the correlation of the graphs with respect to a first parameter, such as time, on the shared first coordinate axis, while displaying each graph with a second coordinate axis having a scale appropriate for the data points plotted in the respective graph. This display of overlaid graphs having different scales for the respective corresponding second coordinate axes according to some embodiments of the invention enables, for example, the display of medical data points defining values having widely different scales in a correlated and visually friendly manner. Clinicians may then be enabled to view trends in each graph line that might not otherwise be viewable if, for example, all of the graph lines were plotted on a single graph having a single scale due to the possibility that a first graph line having relatively small data point values and/or little variation in data point values compared to a second graph line may appear compressed such that it may be hard for a clinician to discern actual values and trends from viewing the first graph line. Embodiments of the invention further enable the correlation of changes in patient condition with changes in patient treatments, thus making a clinician's job easier, and possibly reducing the occurrence of errors in interpretation of medical data.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method for visually presenting medical data to facilitate analysis of the medical data, the method comprising:
   accessing a first set of data points defining medical data values associated with a patient;
   plotting, by a hardware processor, a plurality of data points from the first set of data points on a first graph layer comprising a first coordinate axis and a second coordinate axis, wherein the second coordinate axis has a first scale and each of the plotted plurality of data points from the first set of data points is plotted with respect to the second coordinate axis based at least in part upon the value of the medical data value defined by the data point;
   causing the first graph layer to be displayed;
   accessing a second set of data points defining medical data values associated with the patient;
   plotting, by the hardware processor, a plurality of data points from the second set of data points on a second graph layer, the second graph layer sharing the first coordinate axis with the first graph layer and further comprising a third coordinate axis, wherein the third coordinate axis has a second scale and each of the plotted plurality of data points from the second set of data points is plotted with respect to the third coordinate axis based at least in part upon the value of the medical data value defined by the data point;
   causing, by the hardware processor, the second graph layer to be displayed overlaying the first graph layer, wherein at least a portion of the second graph layer is semi-transparent such that at least a portion of the first graph layer underlying the second graph layer is viewable concurrently with the second graph layer;
   receiving an indication to move the first set of data points to the second graph layer;
   in response to the indication, moving the first set of data points to the second graph layer at least in part by adjusting a transparency of the first set of data points to match a transparency of the second graph layer,
   wherein the second graph layer is defined by a geometric shape, the geometric shape having a perimeter defining an interior portion of the geometric shape, wherein the plurality of points from the second set of data are plotted within the interior portion, and wherein the interior portion is semi-transparent to enable at least a portion of the first graph layer to be viewable concurrently with the second graph layer.

2. The method of claim 1, wherein:
each data point of the first set of data points is associated with a time at which the medical data value defined by the data point was captured;
each data point of the second set of data points is associated with a time at which the medical data value defined by the data point was captured;
the first coordinate axis defines a period of time;
plotting the plurality of data points from the first set of data points comprises plotting each of the plotted plurality of data points from the first set of data points with respect to the first coordinate axis based at least in part upon the time at which the medical data value defined by the data point was captured; and
plotting the plurality of data points from the second set of data points comprises plotting each of the plotted plurality of data points from the second set of data points with respect to the first coordinate axis based at least in part upon the time at which the medical data value defined by the data point was captured such that the plotted plurality of data points from the second set of data points are time correlated with the plotted plurality of data points from the first set of data points.

3. The method of claim 2, further comprising:
adjusting one or more of the period of time defined by the first axis or a scale of the first axis to change a field of view displayed by the displayed first and second graph layers.

4. The method of claim 1, wherein one of the first set of data points or the second set of data points defines medical data values related to a condition of the patient and the other set of data points defines medical data values related to treatment administered to the patient.

5. The method of claim 1, further comprising:
determining a selection of a plotted data point; and
causing the medical data value defined by the selected plotted data point to be displayed.

6. The method of claim 1, further comprising:
determining a selection of the first set of data points; and
determining a selection of the second set of data points; wherein:
accessing the first set of data points comprises accessing the first set of data points in response to determining the selection of the first set of data points; and
accessing the second set of data points comprises accessing the second set of data points in response to determining the selection of the second set of data points.

7. The method of claim 1, further comprising:
reordering display of the first graph layer and the second graph layer such that the first graph layer is displayed overlaying the second graph layer, wherein in the reordered display, the first graph layer is semi-transparent such that at least a portion of the second graph layer underlying the first graph layer is viewable concurrently with the first graph layer.

8. The method of claim 1, wherein a plurality of data points from a third set of data points are plotted on the first graph layer, the method further comprising, responsive to a user request:
moving the plotted plurality of data points from the third set of data points from the first graph layer to a third graph layer, the plotted plurality of data points from the first data set remaining plotted on the first graph layer, the third graph layer sharing the first coordinate axis with the first graph layer and further comprising a fourth coordinate axis, wherein the fourth coordinate axis has a third scale and each of the plotted plurality of data points from the third set of data points is plotted with respect to the fourth coordinate axis; and
causing the third graph layer to be displayed overlaying the first graph layer, wherein at least a portion of the third graph layer is semi-transparent such that at least a portion of the first graph layer underlying the third graph layer is viewable concurrently with the third graph layer.

9. The method of claim 1, wherein one of the first set of data points or the second set of data points defines medical data values related to a condition of the patient and the other set of data points defines medical data values defining a quantity of a medication administered to the patient.

10. The method of claim 1, wherein one of the first set of data points or the second set of data points defines medical data values related to a condition of the patient and the other set of data points defines medical data values defining treatment setting values for a treatment administered to the patient.

11. An apparatus for visually presenting medical data to facilitate analysis of the medical data, the apparatus comprising a processor configured to cause the apparatus to:
access a first set of data points defining medical data values associated with a patient;
plot a plurality of data points from the first set of data points on a first graph layer comprising a first coordinate axis and a second coordinate axis, wherein the second coordinate axis has a first scale and each of the plotted plurality of data points from the first set of data points is plotted with respect to the second coordinate axis based at least in part upon the value of the medical data value defined by the data point;
cause the first graph layer to be displayed;
access a second set of data points defining medical data values associated with the patient;
plot a plurality of data points from the second set of data points on a second graph layer, the second graph layer sharing the first coordinate axis with the first graph layer and further comprising a third coordinate axis, wherein the third coordinate axis has a second scale and each of the plotted plurality of data points from the second set of data points is plotted with respect to the third coordinate axis based at least in part upon the value of the medical data value defined by the data point;
cause the second graph layer to be displayed overlaying the first graph layer, wherein at least a portion of the second graph layer is semi-transparent such that at least a portion of the first graph layer underlying the second graph layer is viewable concurrently with the second graph layer;
receive an indication to move the first set of data points to the second graph layer; and
in response to the indication, move the first set of data points to the second graph layer at least in part by adjusting a transparency of the first set of data points to match a transparency of the second graph layer,
wherein the second graph layer is defined by a geometric shape, the geometric shape having a perimeter defining an interior portion of the geometric shape, wherein the plurality of points from the second set of data are plotted within the interior portion, and wherein the interior portion is semi-transparent to enable at least a portion of the first graph layer to be viewable concurrently with the second graph layer.

12. The apparatus of claim 11, wherein:
each data point of the first set of data points is associated with a time at which the medical data value defined by the data point was captured;

each data point of the second set of data points is associated with a time at which the medical data value defined by the data point was captured;

the first coordinate axis defines a period of time;

the processor is configured to cause the apparatus to plot the plurality of data points from the first set of data points by plotting each of the plotted plurality of data points from the first set of data points with respect to the first coordinate axis based at least in part upon the time at which the medical data value defined by the data point was captured; and the processor is configured to cause the apparatus to plot the plurality of data points from the second set of data points by plotting each of the plotted plurality of data points from the second set of data points with respect to the first coordinate axis based at least in part upon the time at which the medical data value defined by the data point was captured such that the plotted plurality of data points from the second set of data points are time correlated with the plotted plurality of data points from the first set of data points.

13. The apparatus of claim 11, wherein the processor is further configured to cause the apparatus to:

adjust one or more of the period of time defined by the first axis or a scale of the first axis to change a field of view displayed by the displayed first and second graph layers.

14. The apparatus of claim 11, wherein one of the first set of data points or the second set of data points defines medical data values related to a condition of the patient and the other set of data points defines medical data values related to treatment administered to the patient.

15. The apparatus of claim 14, wherein the medical data values related to a condition of the patient define one or more of input values, output values, patient reported values, central venous pressure values, internal pressure measurement values, lab values, blood pressure values, oxygen saturation percentage values, body temperature values, pulse rate values, heart rate values, or respiratory rate values of the patient.

16. The apparatus of claim 14, wherein the medical data values related to treatment administered to the patient define one or more of input values, ventilator settings, quantity of a medication administered to the patient, or medication drip settings.

17. The apparatus of claim 11, wherein the processor is further configured to cause the apparatus to:

determine a selection of a plotted data point; and cause the medical data value defined by the selected plotted data point to be displayed.

18. The apparatus of claim 11, further comprising at least one memory storing instructions that when executed by the processor cause the apparatus to:

access a first set of data points defining medical data values associated with a patient;

plot a plurality of data points from the first set of data points on a first graph layer comprising a first coordinate axis and a second coordinate axis, wherein the second coordinate axis has a first scale and each of the plotted plurality of data points from the first set of data points is plotted with respect to the second coordinate axis based at least in part upon the value of the medical data value defined by the data point;

cause the first graph layer to be displayed;

access a second set of data points defining medical data values associated with the patient;

plot a plurality of data points from the second set of data points on a second graph layer, the second graph layer sharing the first coordinate axis with the first graph and further comprising a third coordinate axis, wherein the third coordinate axis has a second scale and each of the plotted plurality of data points from the second set of data points is plotted with respect to the third coordinate axis based at least in part upon the value of the medical data value defined by the data point; and cause the second graph layer to be displayed overlaying the first graph layer, wherein at least a portion of the second graph layer is semi-transparent such that at least a portion of the first graph layer underlying the second graph layer is viewable concurrently with the second graph layer.

19. A computer program product comprising at least one non-transitory computer-readable storage medium having computer-readable program instructions stored therein, the computer-readable program instructions comprising:

program instructions configured to access a first set of data points defining medical data values associated with a patient;

program instructions configured to plot a plurality of data points from the first set of data points on a first graph layer comprising a first coordinate axis and a second coordinate axis, wherein the second coordinate axis has a first scale and each of the plotted plurality of data points from the first set of data points is plotted with respect to the second coordinate axis based at least in part upon the value of the medical data value defined by the data point;

program instructions configured to cause the first graph layer to be displayed;

program instructions configured to access a second set of data points defining medical data values associated with the patient;

program instructions configured to plot a plurality of data points from the second set of data points on a second graph layer, the second graph layer sharing the first coordinate axis with the first graph layer and further comprising a third coordinate axis, wherein the third coordinate axis has a second scale and each of the plotted plurality of data points from the second set of data points is plotted with respect to the third coordinate axis based at least in part upon the value of the medical data value defined by the data point;

program instructions configured to cause the second graph layer to be displayed overlaying the first graph layer, wherein at least a portion of the second graph layer is semi-transparent such that at least a portion of the first graph layer underlying the second graph layer is viewable concurrently with the second graph layer;

program instructions configured to receive an indication to move the first set of data points to the second graph layer; and program instructions configured to, in response to the indication, move the first set of data points to the second graph layer at least in part by adjusting a transparency of the first set of data points to match a transparency of the second graph layer, wherein the second graph layer is defined by a geometric shape, the geometric shape having a perimeter defining an interior portion of the geometric shape, wherein the plurality of points from the second set of data are plotted within the interior portion, and wherein the interior portion is semi-transparent to enable at least a portion of the first graph layer to be viewable concurrently with the second graph layer.

20. The computer program product of claim 19, wherein:
- each data point of the first set of data points is associated with a time at which the medical data value defined by the data point was captured;
- each data point of the second set of data points is associated with a time at which the medical data value defined by the data point was captured;
- the first coordinate axis defines a period of time;
- the program instruction configured for plotting the plurality of data points from the first set of data points comprises instructions configured for plotting each of the plotted plurality of data points from the first set of data points with respect to the first coordinate axis based at least in part upon the time at which the medical data value defined by the data point was captured; and
- the program instruction configured for plotting the plurality of data points from the second set of data points comprises instructions configured for plotting each of the plotted plurality of data points from the second set of data points with respect to the first coordinate axis based at least in part upon the time at which the medical data value defined by the data point was captured such that the plotted plurality of data points from the second set of data points are time correlated with the plotted plurality of data points from the first set of data points.

21. The computer program product of claim 19, wherein one of the first set of data points or the second set of data points defines medical data values related to a condition of the patient and the other set of data points defines medical data values related to treatment administered to the patient.

* * * * *